(12) United States Patent
Krnc

(10) Patent No.: US 8,601,617 B1
(45) Date of Patent: Dec. 10, 2013

(54) MOUNTING DEVICE FOR ATTACHING A DEVICE TO A MASK

(75) Inventor: Michael Krnc, Medina, OH (US)

(73) Assignee: Advanced Basic Communications, Beachwood, OH (US)

( * ) Notice: Subject to any disclaimer, the term of this patent is extended or adjusted under 35 U.S.C. 154(b) by 738 days.

(21) Appl. No.: 12/577,107

(22) Filed: Oct. 9, 2009

Related U.S. Application Data

(60) Provisional application No. 61/104,700, filed on Oct. 11, 2008.

(51) Int. Cl.
*A61F 9/02* (2006.01)

(52) U.S. Cl.
USPC .................. 2/443; 2/410; 2/455; 128/200.24

(58) Field of Classification Search
USPC ............. 2/429, 431, 428, 443, 448, 422, 441, 2/424, 455, 9, 10, 410; 24/616, 625; 351/116; 128/200.24, 201.14, 201.23, 128/201.15
See application file for complete search history.

(56) References Cited

U.S. PATENT DOCUMENTS

| | | | | |
|---|---|---|---|---|
| 4,639,982 A * | 2/1987 | Kasai | ............................. | 24/616 |
| 4,712,280 A * | 12/1987 | Fildan | ............................. | 24/625 |
| 5,027,443 A * | 7/1991 | Watkins | ............................ | 2/437 |
| 5,410,763 A * | 5/1995 | Bolle | ............................. | 2/436 |
| 5,590,444 A * | 1/1997 | Krauss | ............................ | 24/625 |
| 5,657,493 A * | 8/1997 | Ferrero et al. | .................. | 2/428 |
| 6,105,177 A * | 8/2000 | Paulson et al. | .................. | 2/431 |
| 6,349,419 B1 * | 2/2002 | Chiang | ............................. | 2/428 |
| 6,405,384 B1 * | 6/2002 | Chiang | ............................. | 2/428 |
| 6,532,603 B1 * | 3/2003 | Lan | ................................. | 2/428 |
| 6,611,965 B1 * | 9/2003 | Lee | ................................. | 2/431 |
| 6,865,753 B2 * | 3/2005 | Nishida | ............................ | 2/426 |
| 7,059,717 B2 * | 6/2006 | Bloch | .......................... | 351/119 |
| 7,100,215 B2 * | 9/2006 | Shiue | ............................... | 2/443 |
| 7,181,780 B1 * | 2/2007 | Chiang | ............................. | 2/452 |
| 7,257,848 B2 * | 8/2007 | Chiang | ............................. | 2/448 |
| 7,604,346 B2 * | 10/2009 | Wang | ............................ | 351/43 |
| 7,647,650 B2 * | 1/2010 | Chiang | ............................. | 2/431 |
| 7,841,345 B2 * | 11/2010 | Guney et al. | ............. | 128/207.11 |
| 8,065,752 B2 * | 11/2011 | Kuroda | ............................. | 2/428 |
| 8,166,575 B2 * | 5/2012 | Haselmayer | ...................... | 2/422 |
| 8,193,940 B2 * | 6/2012 | Cummings et al. | ........ | 340/572.8 |
| 2003/0019018 A1 * | 1/2003 | Markovitz | ........................ | 2/441 |
| 2005/0036103 A1 * | 2/2005 | Bloch | .......................... | 351/116 |

\* cited by examiner

*Primary Examiner* — Richale Quinn

(74) *Attorney, Agent, or Firm* — Edwin A. Sisson, Attorney at Law, LLC

(57) ABSTRACT

Disclosed in this specification is a mounting device to mount or attach various types of mounted devices, including a data transmission device, to a mask. The mounting device does not destroy or alter the seal integrity of the mask.

3 Claims, 13 Drawing Sheets

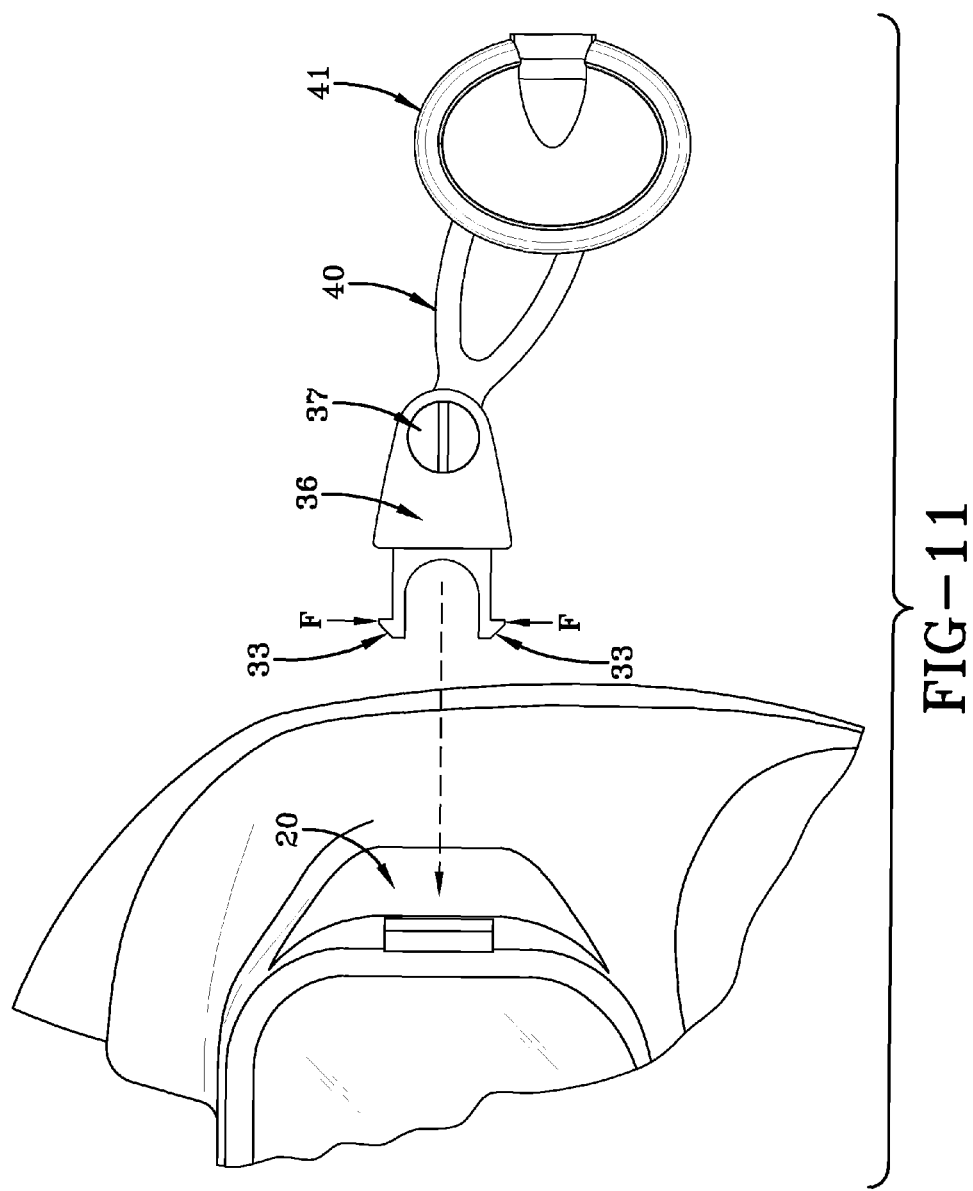

MOUNTING DEVICE FOR ATTACHING A DEVICE TO A MASK

PRIORITY AND CROSS REFERENCES

This application claims priority from U.S. provisional application No. 61/104,700, titled MOUNTING DEVICE FOR ATTACHING A DEVICE TO A MASK, filed 10 Oct. 2008.

BACKGROUND

Masks, in particular gas masks or self contained breathing apparatuses, have become increasingly complex.

These masks form an integral seal around the user's face to prevent vapors in the atmosphere from reaching the user's eyes, nose, mouth or skin surrounded by the mask. A full mask, or full face mask, will protect all the numerated parts. A partial mask, or half mask, will protect the eyes and the skin surrounded by the mask or the nose, mouth and skin surrounded by the mask.

For extreme and unpredictable conditions, such as those experienced by firefighters, police officers, and military; the full face mask is preferred. Because the masks may be worn for an extended period of time, several modifications have been made to allow the user to communicate and even receive nutrients and water without removing the mask. The full mask usually has at least one air filter port to which a filter is attached. The filter removes the contaminants from the air and allows the user to breathe uncontaminated air. In the case of a self contained apparatus, the air is provided from a bottle and no filter is needed.

Over time, the gas mask has evolved to include physical and electronic ports. For example, Avon Products series 50 (manufactured in Cadillac, Mich.), has a tube and twistable spout for the user to receive a liquid without breaking the seal. The Avon products 50, 51, and 53 series of masks use an outsert lens as described in the specification below. Some of Avon Products masks also have a communications device for the user to speak into and the sound is audibly heard outside the mask or sent to a transmission device for reception at another spot.

Masks prior to the Avon Products M50 began including a transmission device to be attached to the port of a dual filter mask, using one of the ports for transmission limits the use time between changing filters.

There is a need for even more devices attached or mounted to the mask. Because the attachment of devices to the mask cannot break the seal integrity of the mask or interfere with hoods worn to cover all the exposed skin, including the mask, unique, inventive devices are needed.

SUMMARY

This specification discloses a mask, comprising at least one outsert attachment member receiver, an outsert, and a mounting device, wherein the outsert attachment member receiver comprises an outsert attachment member receiving hole, with the outsert attachment receiver hole further comprising a first end and a second end, wherein the outsert comprises an outsert attachment member passing through the first end of the at least one outsert attachment receiver, and the mounting device comprises a mounting device attachment member passing through the second end of the at least one outsert attachment receiver.

A method of attaching a mounted device is further disclosed. The method of attaching a mounted device to a mask comprises the steps of; inserting an outsert attachment member of an outsert into an outsert attachment member receiver of the mask until the outsert attachment member is fixed; inserting a mounting device attachment member having a mounted device attached to the mounting device, into the outsert attachment member receiver.

An alternate method of attaching a mounted device to a mask is disclosed, wherein said method comprises the steps of; inserting an outsert attachment member of an outsert into an outsert attachment member receiver of the mask until the outsert attachment member is fixed; inserting a mounting device attachment member, into the outsert attachment member receiver, and attaching a mounted device to the mounting device.

BRIEF DESCRIPTION OF FIGURES

FIG. 11 depicts the embodiment of FIG. 9 disassembled from and relative to the gas mask.

DETAILED DESCRIPTION

The apparatus claimed in this specification is a mask, wherein the mask has an outsert attachment member receiver, with a mounting device attached to the mask, wherein the mounting device is uniquely modified to be attached to the mask at the outsert attachment receiver without destroying the seal integrity of the mask, and preferably in most instances, not even modifying the mask itself. The mounting device, once mounted or attached to the mask, can have other devices attached to it as well.

The mounting device takes unique advantage of the outsert attachment member receiver usually molded as part of the mask's special plastic material. Current mounting devices replace the mounting spot of a current component with the new component. An example of this loss is when a filter is removed from its mounting port and the new device mounted in the port instead. Unlike the current mounting devices which replace the mounting device of a current component for the new component the mounting device of this specification does not cause the user to lose functionality of a current device.

Figure 1:
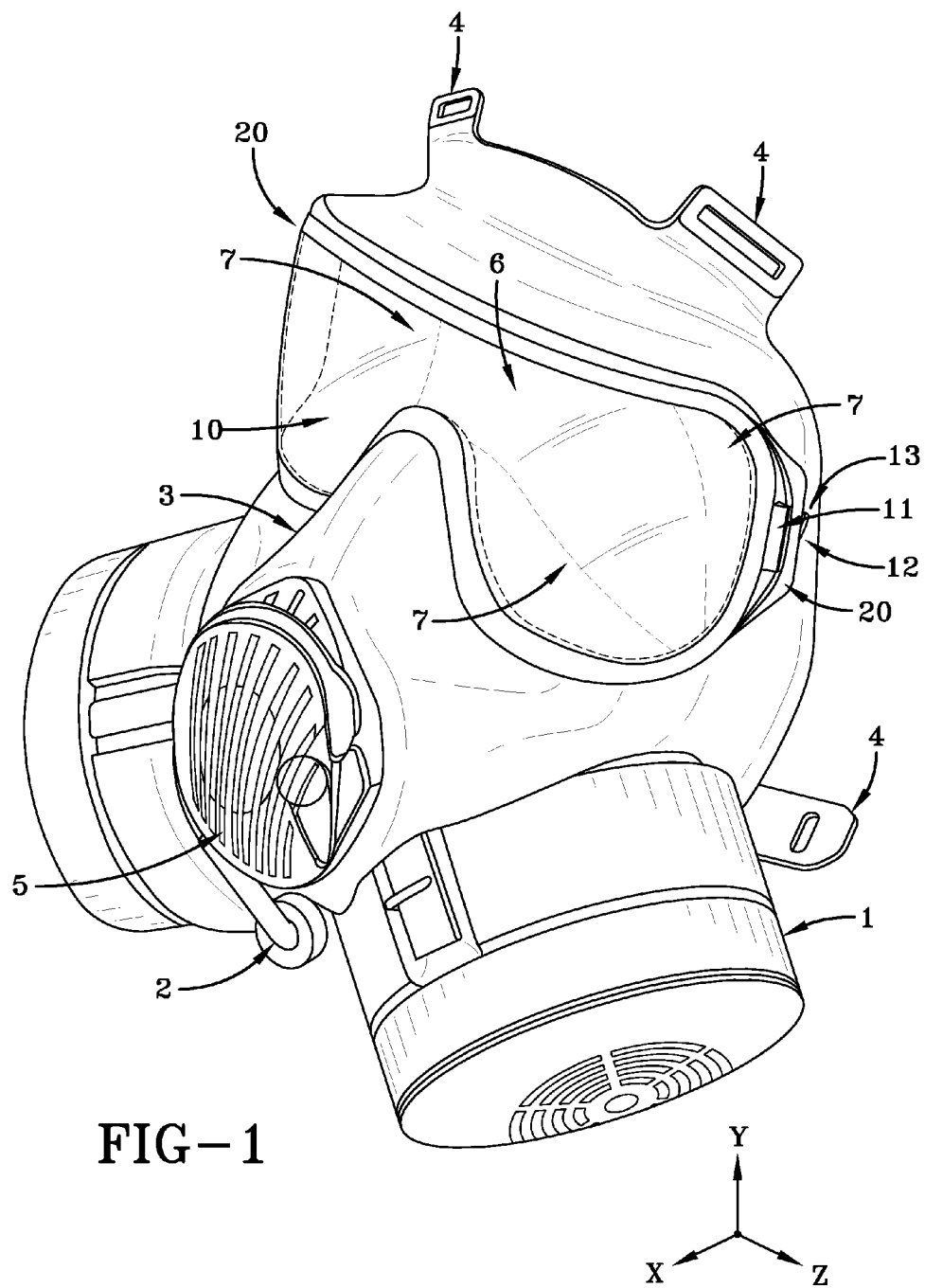
FIG. 1 depicts an example of a currently used mask without the attachment device.

FIG. 1 is an example of one the currently available masks. There are two filters (1) which allow clean air to enter the mask by passing the air through a filter medium. A tube (2) allows liquid to be passed into the mask. The nosepiece is depicted as numeral 3. The straps holding the mask fit into the slots depicted as numeral 4 are where the harness or other straps are attached to fit the mask snugly around the user's face. The object labeled 5 is the mouthpiece which amplifies sounds spoken inside the mask.

It should be noted that for the purposes of this specifications, the numbering is consistent from figure to figure. For example, the element labeled 10 in FIG. 1 will correspond to the element labeled 10 in any of the other Figures.

Masks which protect the eyes will have a viewing lens (6) usually made of a transparent plastic or glass through which the wearer can see. The viewing lens (6) is often directly molded into the plastic of the mask to provide more durable eye protection. The viewing lens is depicted as numeral 6 with the edges of the viewing lens shown as the dashed lines labeled 7. The viewing lens (6) is often molded into the mask to provide a better seal. This molding would occur at the dashed lines labeled 7. Viewing lens (6) is located behind the outsert lens (10) relative to the X axis (See FIG. 2 for axis orientation).

Many masks with and without a viewing lens (6) or viewing lenses, if using a split lens configuration, are designed to accommodate an outsert lens or an outsert which is depicted as numeral 10 in FIG. 1 and subsequent figures. The outsert lens (10) attaches to the mask and protects the viewing lens (6) from scratches and coming in contact with other objects. The outsert (10) can be tinted to offer the user the ability to filter various lights without having to change the viewing lens. For example, the outsert lens (10) could be tinted to block sunlight or ultraviolet rays. The outsert could be tinted to accommodate laser and night vision infrared lights. It is noted that numbers 10 through 19 apply to parts of an outsert lens, also called the outsert.

The outsert lens (10) comprises an outsert attachment member depicted as 11 in FIG. 1 and subsequent figures. Arrow 11 it is to depict the whole outsert attachment member as defined in this specification. This includes the point of the outsert attachment member labeled 12 (See FIG. 2 as well) which is the pointed end of the outsert attachment member. The outsert lens (10) is attached or fixed to the mask using the outsert attachment member receiver (20) of the mask. As shown in FIG. 1, the outsert attachment member (11) passes through the outsert attachment member receiver (20).

Figure 2:
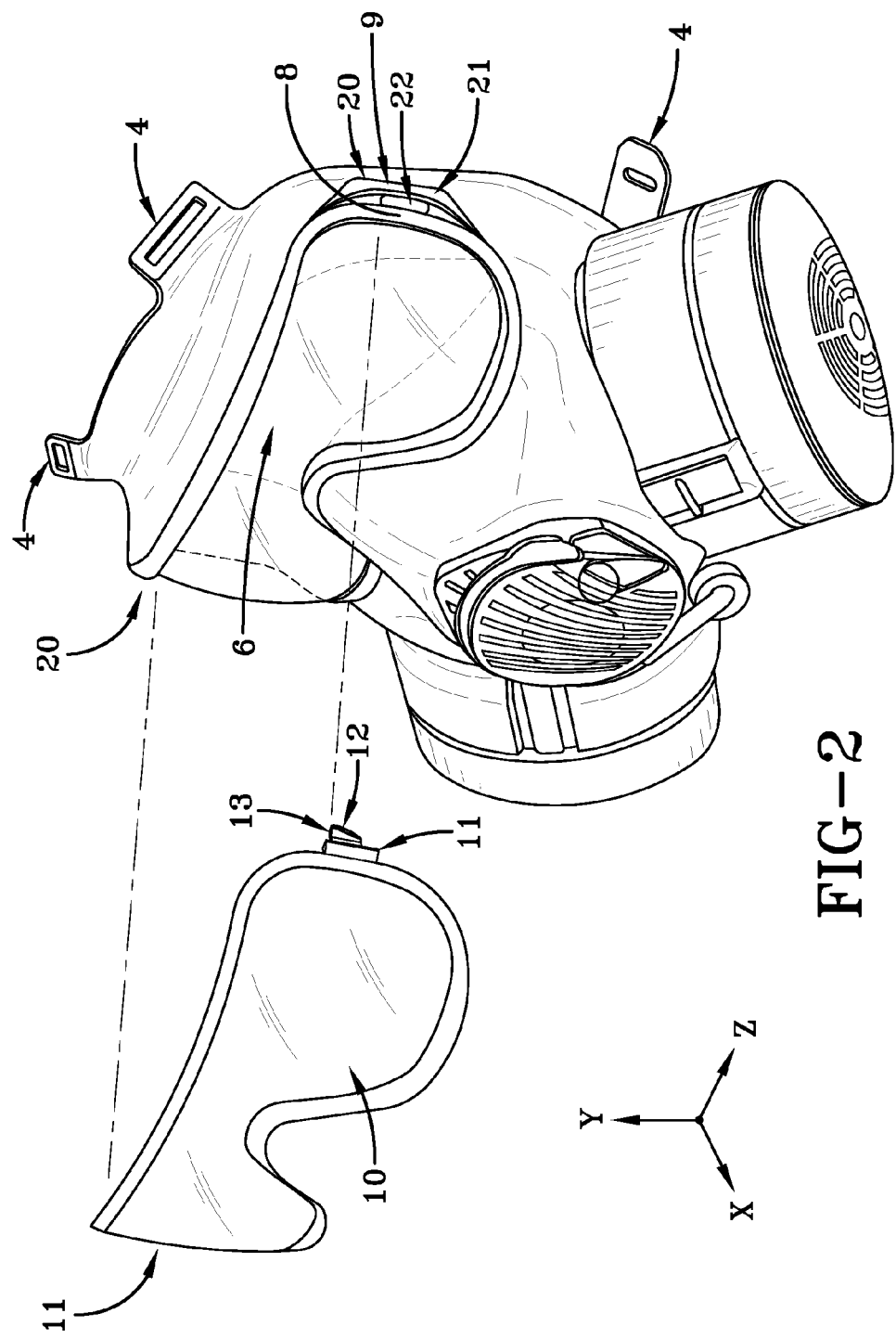
FIG. 2 depicts a currently used mask with the outsert removed.

As shown in FIG. 2, the outsert (10) is detachable from the mask. In the embodiment shown, the outsert has an outsert attachment member (11) which is part of the molded outsert (10). In this embodiment, there are two outsert attachment members (11). One is on the side facing the viewer; the other is hidden from view, and is on the side hidden from view along the Z axis. In shown embodiment, FIG. 2, the outsert attachment member comprises a tab which has a slanted member (13) slanting in the direction of the Y axis and comprises a point at the end (12).

The outsert attachment members (11) are spatially located so as to align and be inserted into the outsert attachment member receivers (20). In the case of FIG. 2, the mask has two attachment member receivers, the first is on the visible side of the mask labeled 20, with the other on the non-visible side of the mask, along the line formed by the Z axis. The number of outsert attachment members and attachment receiving members do not have to be the same. The outsert attachment member (11) is inserted into the outsert attachment member receiver of the mask (20).

In the shown embodiment, the outsert attachment member receiver is part of the mask molding with a rigid base (8) and holding member (9). As shown initially in FIG. 2, there is a hole (21) or slot (21) called the outsert attachment member receiver hole (21) or, alternatively, outsert attachment member receiver slot (21) passing through and forming part of the outsert attachment member receiver (20). The Outsert attachment member receiver hole (21) or, alternatively, outsert attachment member receiver slot (21) of the outsert attachment member receiver, has a first end (22) and second end (23) corresponding with the numbers shown in FIG. 4. In the shown embodiment, the outsert attachment member (11) of the outsert lens (10) is inserted into the first end (22) of the outsert attachment member receiver hole (21) of the outsert attachment member receiver (20) until the outsert attachment member (11) has reached the point where it is fixed or locked into place. In the current embodiment, this is the point where the slant (13) on the outsert attachment member (11) passes through the first end hole (22) of the outsert attachment member receiver (20) and protrudes past the second end (23) of the hole (21) or slot (21) of the outsert attachment member receiver (20).

Since the slanted member (13) on the end of the outsert attachment member (11) defines a hole larger than the natural hole defined by the outsert attachment member receiver hole (21) or, alternatively, outsert attachment member receiver slot (21) of the outsert attachment member receiver (20), the outsert attachment member (11) is fixed or locked into place because the outsert attachment member (11) of the outsert lens (10) cannot be removed from the outsert attachment member receiver (20) without distorting the size of the natural hole of the outsert attachment member receiver hole (21) or, alternatively, outsert attachment member receiver hole (21) of the outsert attachment member receiver (20).

In this manner, the outsert lens (10) stays mounted or attached to the mask until someone, usually the user, wants to remove outsert (10). One of ordinary skill will recognize there can be many outsert attachment members of the outsert and many outsert attachment member receivers on the mask. While the embodiment shown in FIG. 2 is for an outsert lens (10) with two attachment members to be attached to two attachment member receivers (20) of the mask, it is quite possible that there could be three outsert attachment members and three outsert attachment member receivers with one located in the center of the top edge or four or fiver outsert attachment members with four or five outsert attachment member receivers.

Figure 3:
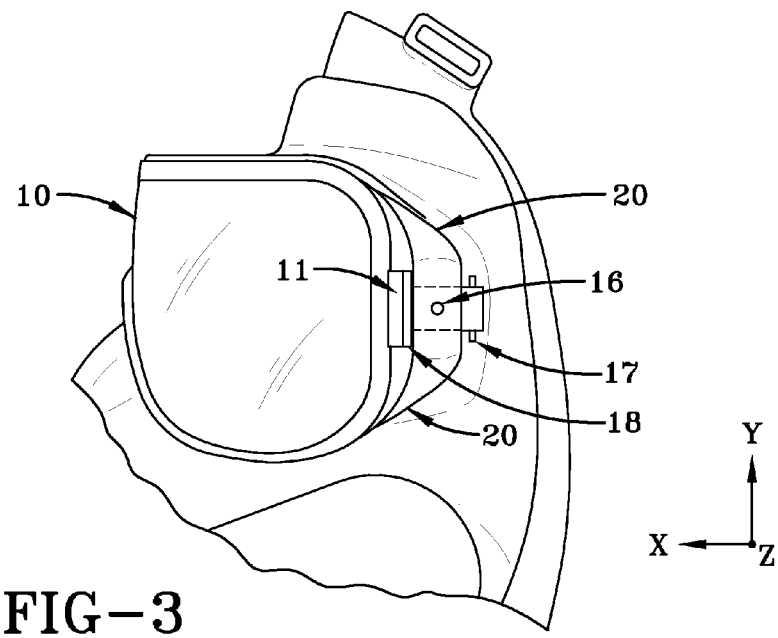
FIG. 3 depicts an alternate embodiment of attaching the outsert to a currently used mask.

There are many other designs for the outsert attachment member (11). The outsert attachment member could be a locking pin (16) which would protrude out a hole in the outsert attachment receiver or a locking rod (17), which would protrude across the natural hole defined by outsert attachment member receiver hole (21) or, alternatively, outsert attachment member receiver slot (21) of the outsert attachment member receiver (20) as shown FIG. 3. The outsert attachment member could be removed by distorting the outsert attachment member receiver so that the natural hole defined outsert attachment member receiver hole (21) or, alternatively, outsert attachment member receiver hole (21) is larger than the locking pin (16) or locking rod (17). Once the natural hole defined by the outsert attachment member receiver hole (21) or, alternatively, the outsert attachment member receiver slot (21) is larger than the locking pin (16) or locking rod (17), the outsert attachment member (11) can be withdrawn from the outsert attachment member (20).

Figure 4:
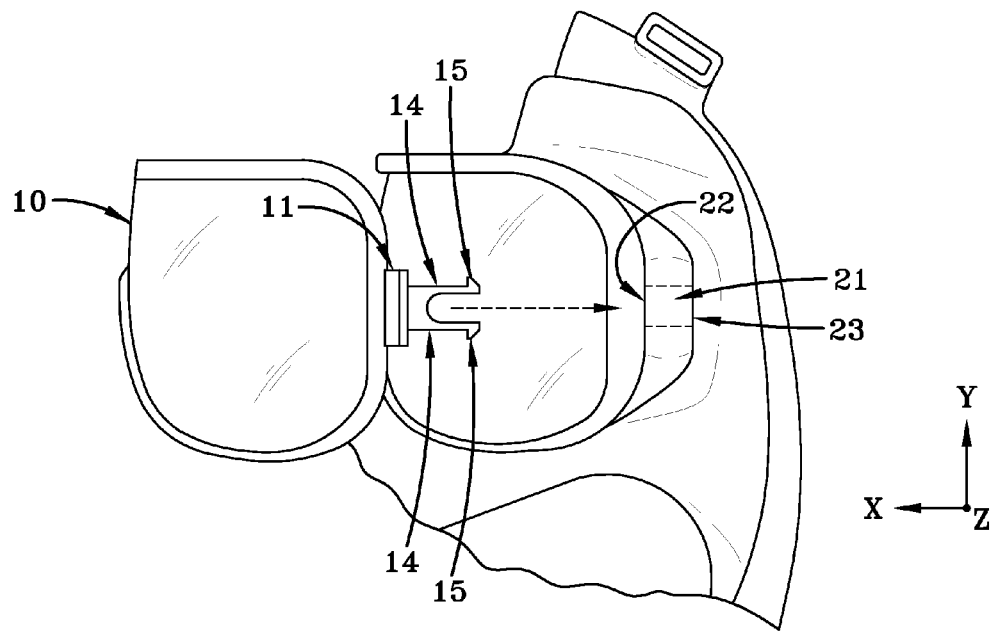
FIG. 4 depicts another alternate embodiment of attaching an outsert lens to a currently used mask.
Figure 5:
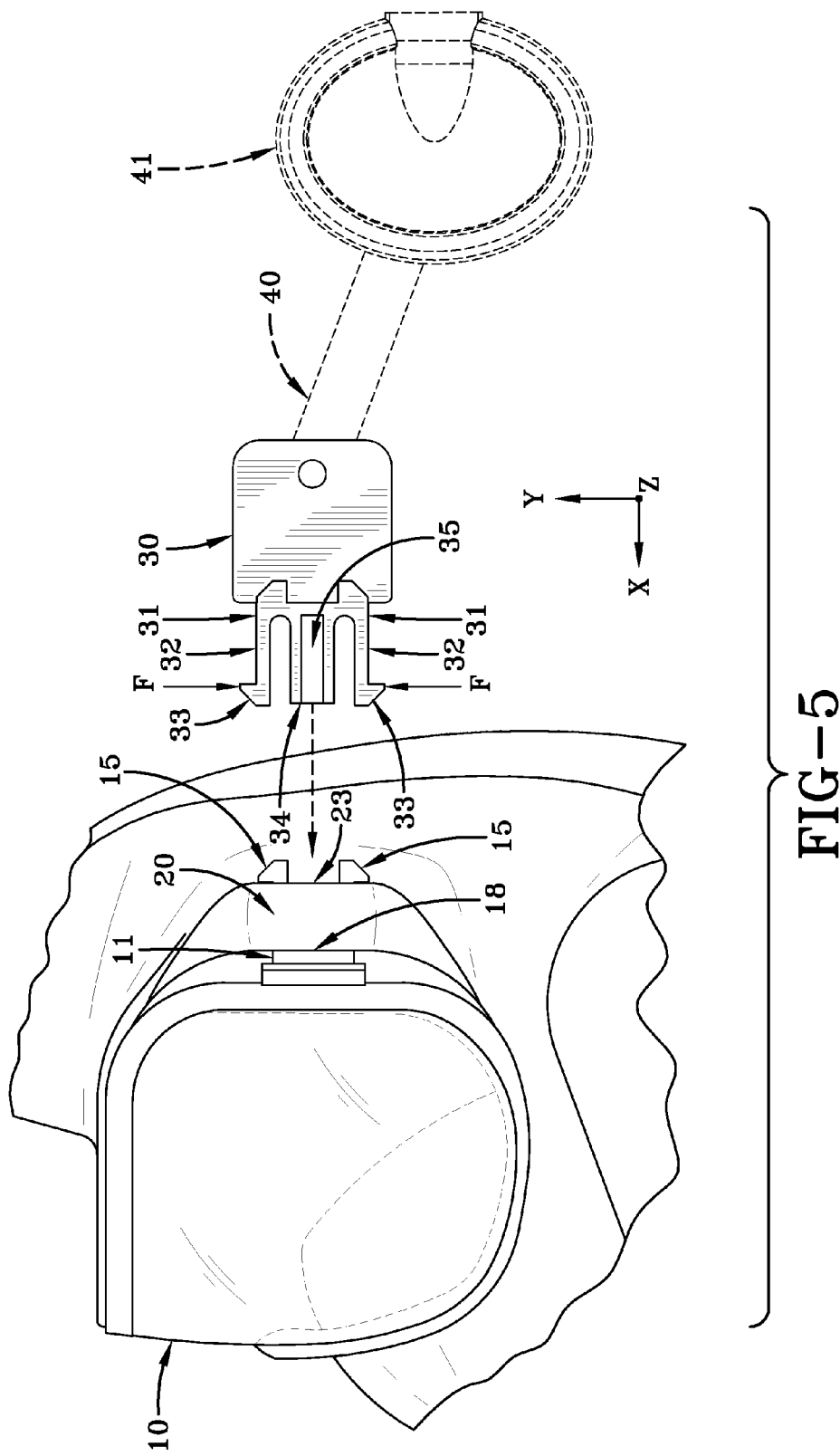
FIG. 5 depicts the currently used mask with the outsert installed in the outsert attachment member of the mask and the mounting device with the mounting device attachment member as well as the mounted device with the mounting device visually detached from the mask.

Another design for the outsert attachment member (11) utilizes pinchable tabs (14) as shown in FIG. 4. In this design, a pinchable tab (14) may have at least one barb (15) and squeeze together with a force F as shown in FIG. 5 as the tabs pass through the hole (21) or slot (21) of the outsert attachment member receiver (20). The point of fixing or locking is generally reached when a barb (15) of a pinchable tab (14) goes beyond hole (21) or slot (21) of the outsert attachment member (20) and the pinchable tabs re-expand, thus fixing or locking the outsert attachment member (11) and subsequently the outsert (10) to the outsert attachment member receiver (20). To remove the outsert attachment member (11), the pinchable tabs (14) are pushed together and pushed back through the second end (23) of the outsert attachment member receiver hole or slot (21) or slot (21) and then passed through the first end (22) of the outsert attachment member receiver hole or slot (21) of the outsert attachment member (20).

When one looks at the mask of FIG. 1 with the outsert (10) attached, there is no unused location to attach another mounting device on the mask. All the mounting locations are used to mount other devices.

It has been discovered that it is possible to use the outsert attachment member receiver (20), in combination with the outsert attachment member (11) of the outsert (10) to provide a mounting or attachment point for a mounting device (numbered 30 in all figures, whose parts are series 30) to mount or attach yet another device, called an attached device (labeled 40, belonging to series 40 in all figures) to the mask. The attached device (40) can be any number of functional devices (41), usually a data transmission device. For example, one may attach an ear piece to transmit sound to the user as shown in FIG. 5. The attached device (40) could also be a monocle or viewing lens which would flip over the viewing point of the outsert so the user could view special visual data or the objects in front of him or her in a different perspective.

FIG. 5 shows an embodiment and is an example of attaching or mounting a data transmission device to the mask and demonstrates the principles of operation of the invention.

One embodiment is the attachment of attached device (40), this case, an ear piece (speaker) to project sound to the ear of the user. The ear piece shown is a type of attached device and depicted by number 40 in FIG. 5. The ear piece is only one type of data transmission device and is necessarily located near the user's ear.

Because the ear piece should stay close to the ear, the ear piece and the mounting device (30) is preferably firmly fixed to keep movement of the ear piece as minimal as possible.

Thus, to keep the movement of the attached device (40) limited, the mounting device (30) is preferably fixed or locked in place in a rather firm manner.

The embodiment in FIG. 5 demonstrates how the problems of attaching another device, without modifying the integrity of the mask and interfering with hoods donned during use of the mask are solved using the following mounting device configuration. It is noted that the numbers 30-39 are reserved for the mounting device (30) used to attach other attached devices (40) to the mask.

In FIG. 5, the outsert attachment member (11), with the barbs (15) of the pinchable tabs, (32) is shown to be inserted in the outsert attachment member receiver (20) by applying force F on the barbs and passing through the first end (22) of the outsert attachment member receiver hole or slot (21) and passing through the second end (23) of the outsert attachment member receiver hole (21) or slot (21), and resting against the outsert attachment member stop (18).

The mounting device (30) has a mounting device attachment member (31) placed into the outsert attachment member receiver (20) though the second end (23) of the hole or slot of the mounting device attachment member (31). In this manner, the mounting device attachment member (31) opposes the direction of the outsert attachment member (11).

The mounting device attachment member (31) can be fixed or locked in many different manners. While it is preferred that the mounting device attachment member (31) not protrude beyond the first end (22) of the outsert attachment member receiver hole (21) of the outsert attachment member receiver (20), protrusion is acceptable and makes the locking or fixing easier.

For example, the outsert attachment member (11) and the mounting device attachment member (31) can be designed to interlock with each other so that the attached device (40) does not unduly move. In the locking mechanism of FIG. 5, which is but one embodiment, the barbed notch (33) keeps the mounting device attachment member (30) from moving in the X direction defined by the travel of the outsert attachment member receiver hole or slot (21) and shown in all Figures. Since the mounting device attachment member (31) is preferably located behind the outsert attachment member relative to the Z axis as shown in 6B, the immobility of the outsert attachment member (11) fixes the mounting device attachment member (31) against the wall of defined by the edge of the outsert attachment member receiver hole or slot (21) of the outsert attachment (20) member and serves to limit the rotation of mounting device attachment member (31) about the Y axis and movement in the positive and negative Z directions as shown on the axis in all Figures.

Figure 6A:
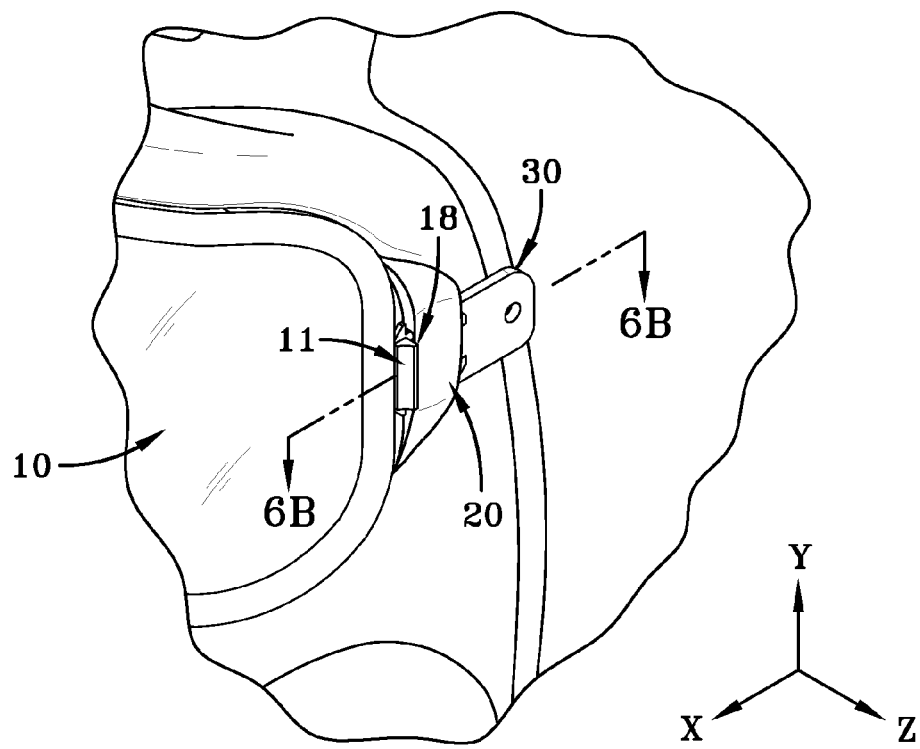
FIG. 6A depicts a mask with the outsert installed in the outsert attachment member of the mask and the mounting device with the mounting device attachment member installed in the attachment member receiver.
Figure 6B:
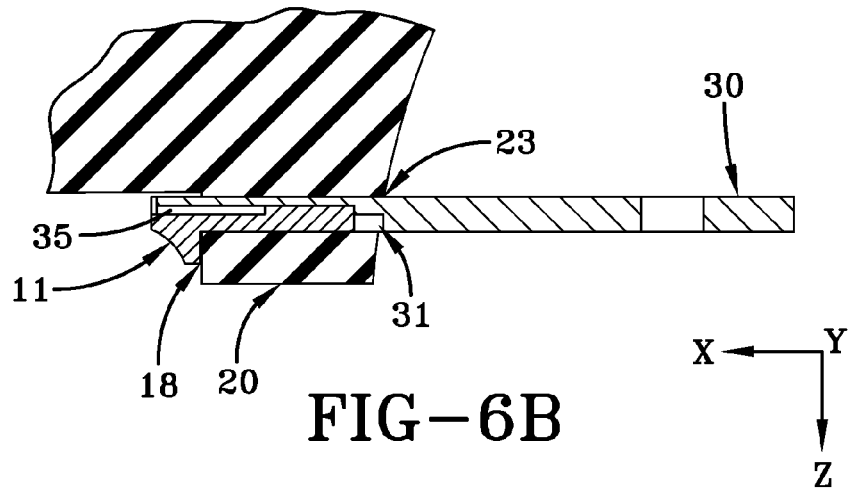
FIG. 6B depicts a cutaway of the mask with the outsert installed in the outsert attachment member of the mask and the mounting device with the mounting device attachment member installed in the attachment member receiver as viewed from the top of the mask in the direction of the arrows pointing to 6B in FIG. 6A.

Rotation of the mounting device attachment member (31) about the Z axis and movement in the positive and negative Y directions can be minimized by the stiffness of the material of construction of the outsert attachment member receiver hole (21) or slot (21) of the outsert attachment member receiver (20) through which the mounting device attachment member (31) has been inserted. Since the stiffness of the mask material may not be enough, a slot and key or tongue and groove design consisting of elements 34 and 35, can be used to keep the Z rotation minimized. In the slot and key design (the slot (34), and the key (35)), the attachment members (11 and 31) of the outsert (10) or the mounting device (30) can have a slot or groove running in the X direction with the attachment member having a key, ridge or tongue of a similar length as the slot or groove and protruding into the slot or groove. The embodiment shown is to place the key (35) on the mounting device attachment member (31). As shown in FIG. 6B, the key (35) fits behind a cutout portion of 11 relative to the X axis preventing travel along the X axis.

Figure 7A:
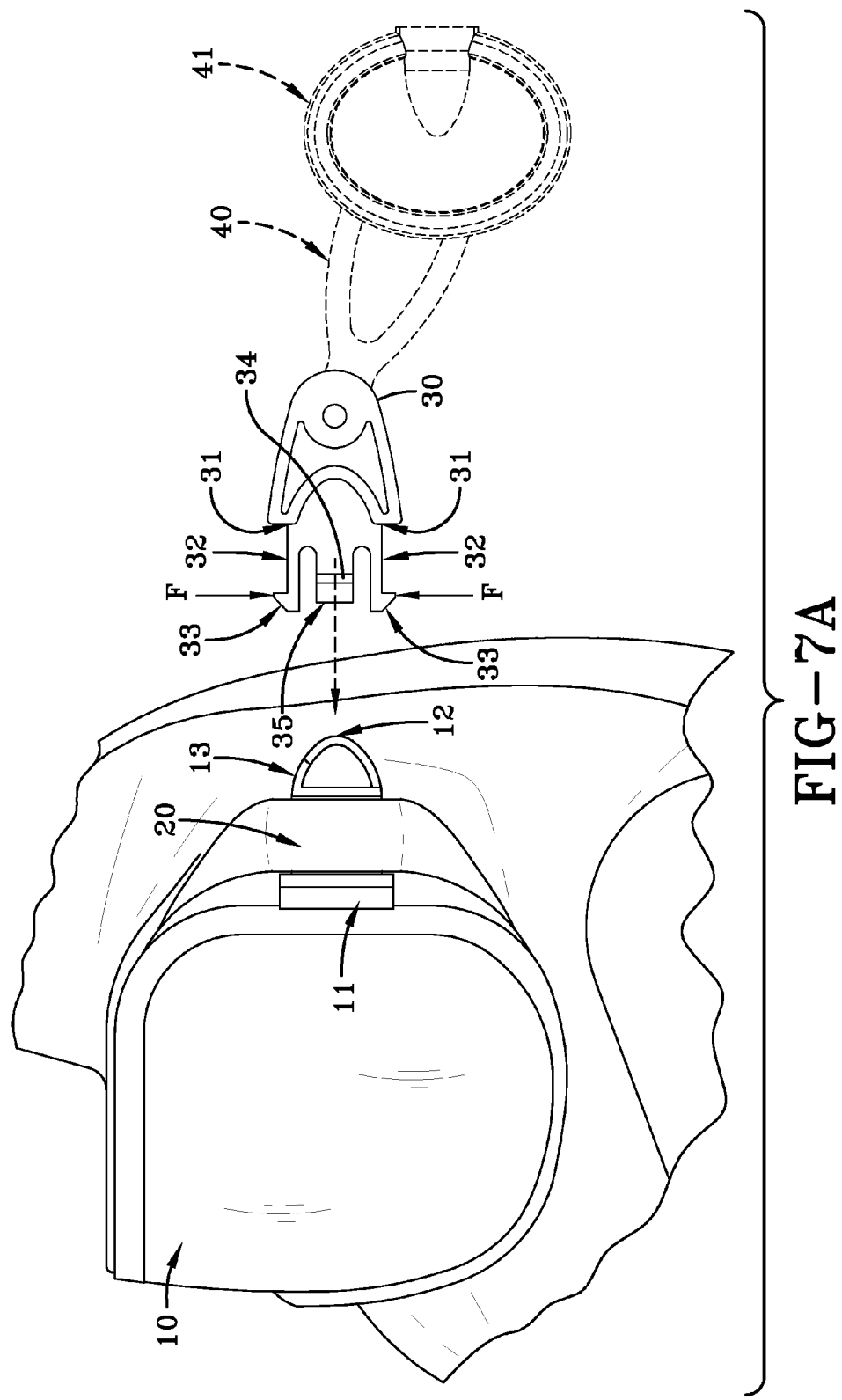
FIG. 7A is another alternate embodiment of attaching the mounting device.
Figure 7C:
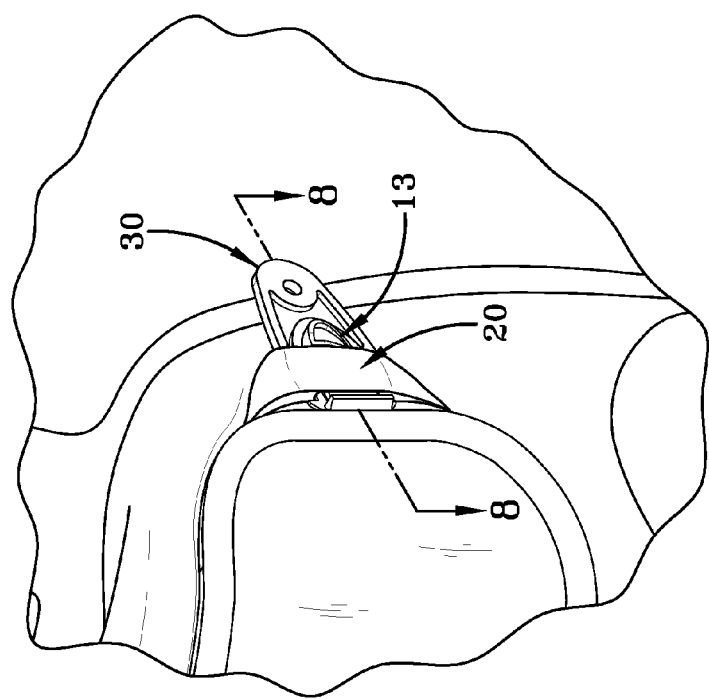
FIGS. 7B and 7C depict an embodiment of the mounting device as it is disassembled and assembled respectively.
Figure 7B:
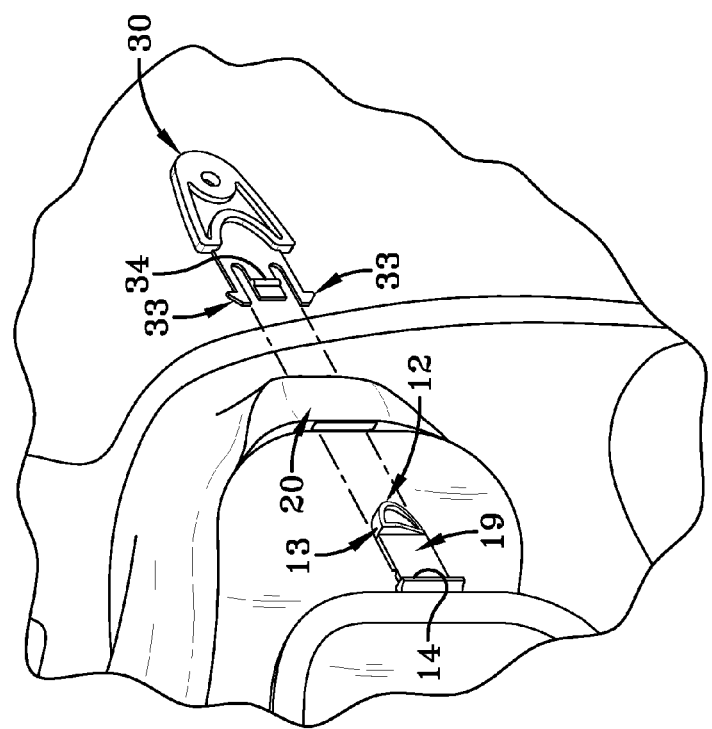
Figure 8:
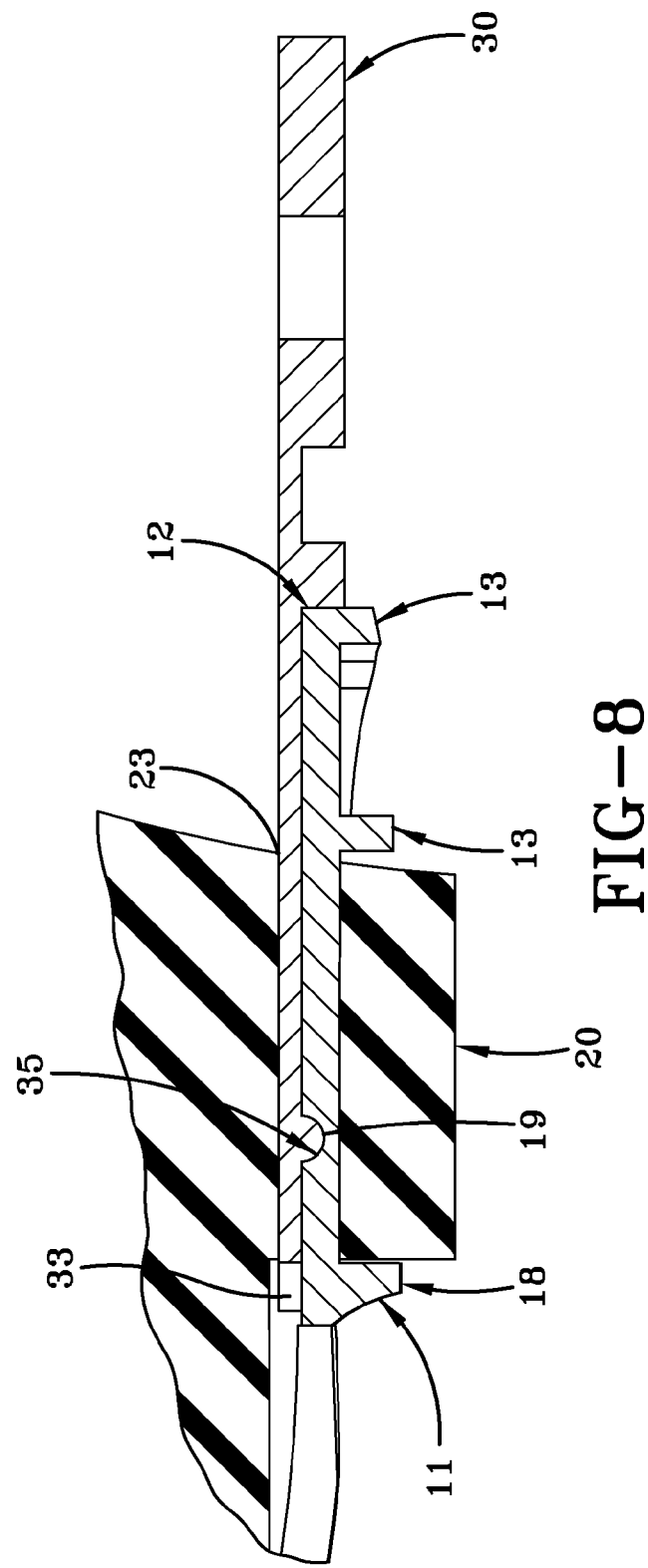
FIG. 8 is the cutaway view of the embodiment of FIGS. 7A, 7B, and 7C.

FIGS. 7 and 8 depict another embodiment of the mounting device. In FIGS. 7A-7C and 8 the outsert is the one depicted in FIG. 2 and the key and slot configuration is rotated 180 degrees from the previous embodiment, so the key (35) is along the Y axis and fits into a groove (19) of the outsert attachment member (FIG. 8). The roundedness of 30 and two prongs of the attached device 40, the functional component of the attached device (41) are further elements. The rounded mating of 30 with 12 of the outsert attachment member helps stabilize the device to movement in the X-Y plane.

FIG. 7B shows how this embodiment is assembled, in particular the locking of key 34 with the notch 19, behind the outsert attachment member receiver (20). FIG. 7B shows the assembled parts, with the cross section shown in FIG. 8.

Figure 9:
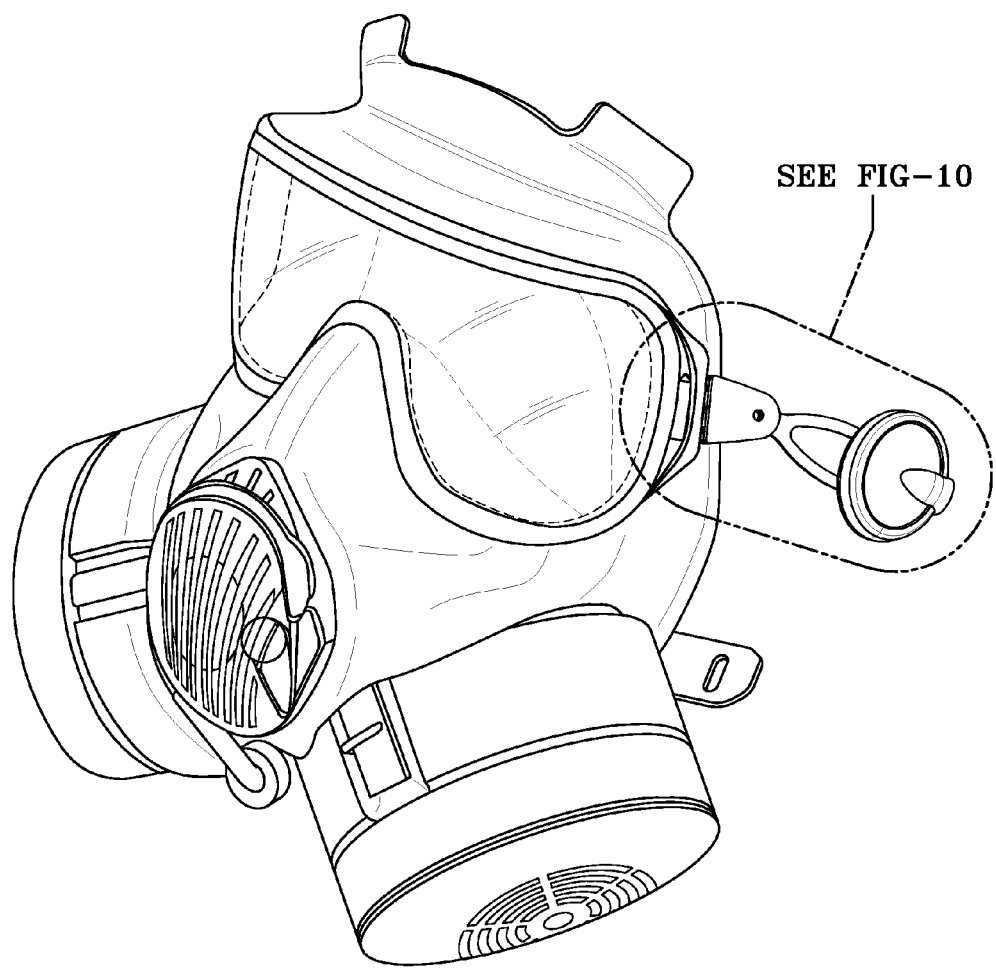
FIG. 9 is depicts another embodiment of the mounting device attached to the mask.
Figure 10:
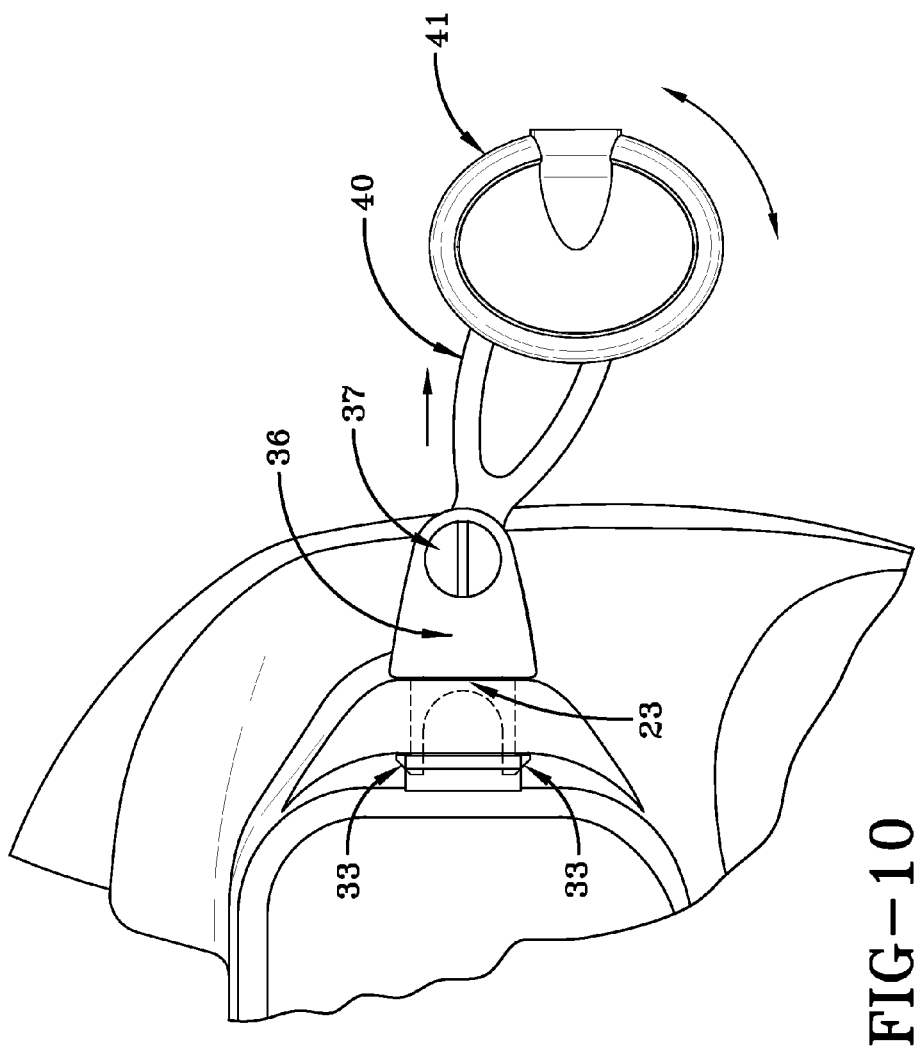
FIG. 10 depicts the embodiment of FIG. 9 in a closer view.

FIGS. 9-12A and 12B depict another embodiment. FIG. 9 is the assembled mask and mounting device. FIG. 10 is magnified view of the circled area in FIG. 9. The two barbed points are depicted as (33) and lie behind the outsert attachment member in the Z direction, but unlike the other embodiments, a mounting device clamp (36) fits over the portion of the outsert attachment member extending past the outsert attachment receiver at 23 and clamps the outsert attachment member between 31 (see FIG. 7A) and the mounting device clamp (36). In this embodiment the parts are kept together with a screw 37. However the attaching device between the mounting device clamp and the mounting device could be any one of attaching devices known in the art and yet to be invented. In this embodiment, the clamp also holds the attached device. As indicate by the arrows, movement and adjustability are permitted by the clamp/screw design.

FIG. 11 depicts the embodiment of FIG. 10 removed from the mask, but with the clamp on showing the snug fit between 20 and the clamp 36.

Figure 12A:
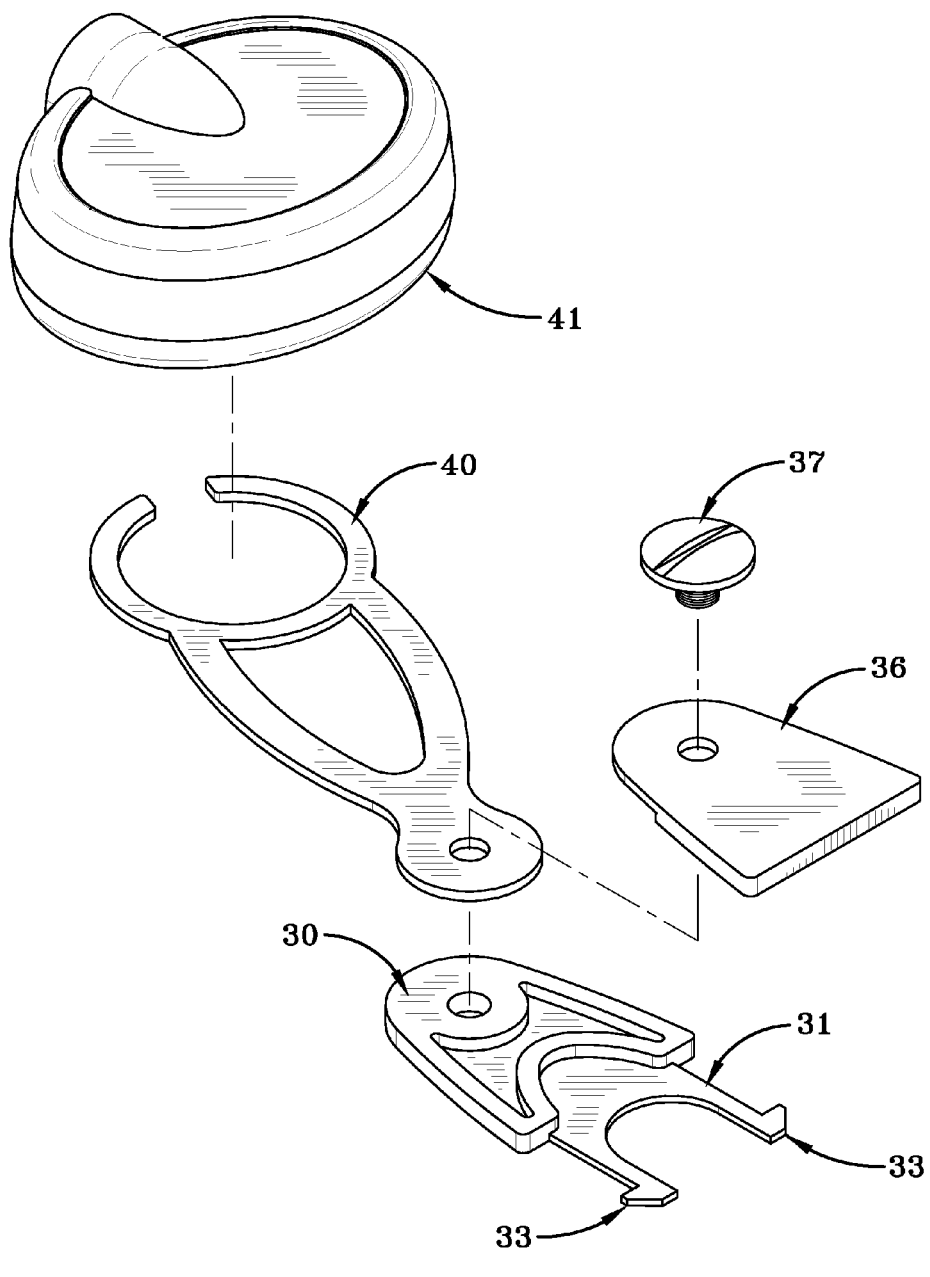
FIG. 12A depicts the disassembled connecting device.

FIG. 12A shows the clamp embodiment disassembled. Note the functional part of the attached device, or mounted device, 41, which in this case is a transmission device, such as an earpiece.

Figure 12B:
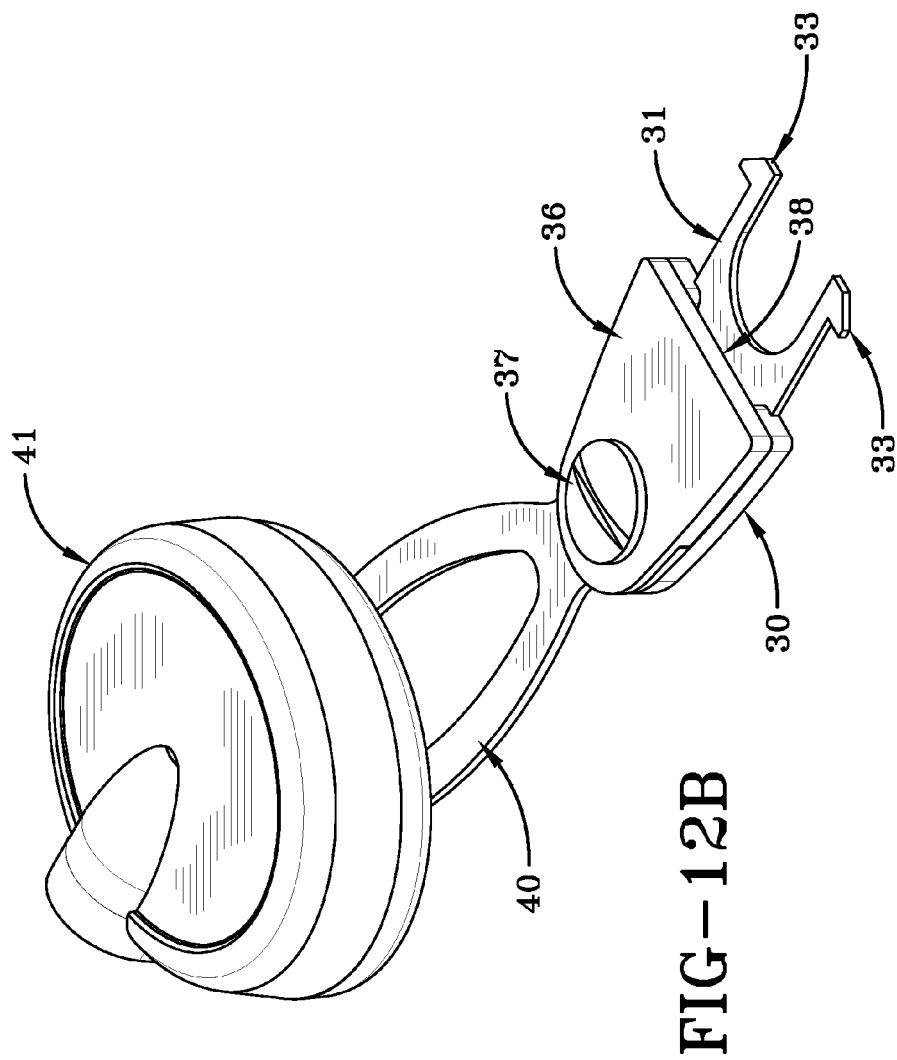
FIG. 12B depicts the mounting device assembled to the transmission device, but not connected to the mask.

FIG. 12B shows a perspective of the clamp embodiment assembled with gap 38 into which the outsert attachment member would extend.

While attaching the mounting device (30) to the mask at a single point, in this case, the outsert attachment member receiver (20), is most efficient, as described earlier, the mounting device could have more than one mounting device attachment member (31). For example, one could mount a more stable night vision goggle that could be flipped down over the outsert lens (10) by utilizing the two attachment member receivers (20) on the mask. In the embodiments shown the other attachment member receiver would be on the other side of the drawing.

Once the mounting device (30) is attached to or mounted on the mask, the claimed apparatus could further comprise any number of attached utilitarian devices. One type of utilitarian device is a data transmission device. Types of data transmission devices include an ear piece, a speaker, a monocle, a light source, a prompter screen, a filter lens, or a magnifying lens. All of the data transmission devices transmit some type of data to the user. For example, the ear piece and speaker transmit sound waves, the monocle transmits visual information, a prompter screen transmits visual data, a filter lens manipulates the viewed light data by removing or adding light data, and the magnifying lens transmits light data that has been manipulated to show enlarged figures to the user. While it is preferred to have the mounting device substantially fixed to the attachment member, the mounting device could further comprise a flexible rod. For the purposes of this specification, the phrase "mounting device further comprises" or "mounting device could further comprise" means that the mounting device has at least one additional comprised element which can be part of the mounting device or detachable from the mounting device. For example, one could mount a flexible rod to the mounting device and attach a monocle that can be rotated over the user's eyes when desired, and rotated out of the way when not desired. The phrase "mounting device further comprises a monocle" would encompass this embodiment because at least one point of stability of the monocle to the mask is an attachment member of a mounting device mounted to an attachment member receiver.

I claim:

1. A mask, comprising at least one outsert lens attachment member receiver, a viewing lens, an outsert lens, and a mounting device,
    wherein the outsert lens attachment member receiver comprises an outsert lens attachment member receiving hole, with the outsert lens attachment member receiving hole further comprising a first end and a second end,
    wherein the outsert lens comprises an outsert lens attachment member passing through the first end of the at least one outsert lens attachment member receiving hole,
    wherein the mounting device comprises a mounting device attachment member passing through the second end of the at least one outsert lens attachment member receiving hole,
    and
    the mask is a gas mask.

2. The mask according to claim 1, wherein the outsert lens attachment member receiver is molded as part of the mask.

3. The mask according to claim 1, wherein the mask further comprises a plurality of utilitarian devices.

\* \* \* \* \*